US007556774B2

(12) United States Patent
Rakow et al.

(10) Patent No.: US 7,556,774 B2
(45) Date of Patent: Jul. 7, 2009

(54) OPTOCHEMICAL SENSOR AND METHOD OF MAKING THE SAME

(75) Inventors: Neal A. Rakow, Woodbury, MN (US); Michael S. Wendland, North St. Paul, MN (US); Michael C. Palazzotto, Woodbury, MN (US); Dora M. Paolucci, St. Paul, MN (US); Richard J. Poirier, White Bear Lake, MN (US); Stefan H. Gryska, Woodbury, MN (US); John E. Trend, St. Paul, MN (US); Moses M. David, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 637 days.

(21) Appl. No.: 11/275,268

(22) Filed: Dec. 21, 2005

(65) Prior Publication Data

US 2007/0140907 A1    Jun. 21, 2007

(51) Int. Cl.
*G01N 21/00* (2006.01)
(52) U.S. Cl. .................. 422/82.05; 422/55; 422/58; 422/60; 422/82.09; 422/86
(58) Field of Classification Search ............... None
See application file for complete search history.

(56) References Cited

U.S. PATENT DOCUMENTS

| 4,776,869 | A  | 10/1988 | Offenbacher et al. |
| 5,015,843 | A  | 5/1991  | Seitz et al.       |
| 5,611,998 | A  | 3/1997  | Aussenegg et al.   |
| 5,783,836 | A  | 7/1998  | Liu et al.         |
| 6,007,904 | A  | 12/1999 | Schwotzer et al.   |
| 6,180,318 | B1 | 1/2001  | Fitzer et al.      |
| 6,396,616 | B1 | 5/2002  | Fitzer et al.      |
| 2004/0062682 | A1 | 4/2004 | Rakow et al. |
| 2004/0184948 | A1 | 9/2004 | Rakow et al. |

(Continued)

FOREIGN PATENT DOCUMENTS

EP    0 665 425 A2    8/1995

(Continued)

OTHER PUBLICATIONS

McKeown et al., "Polymers of Intrinsic Microporosity (PIMS): Bridging the Void between Microporous and Polymeric Materials", Chemistry, A European Journal, 2005, vol. 11, pp. 2610-2620.

(Continued)

*Primary Examiner*—Yelena G Gakh
*Assistant Examiner*—Robert Xu
(74) *Attorney, Agent, or Firm*—Bradford B. Wright

(57) ABSTRACT

A method of making an optochemical sensor, the method comprising: providing a reflective substrate having a major surface; affixing a detection layer comprising at least one intrinsically microporous polymer to at least a portion of the major surface; depositing a substantially continuous semi-reflective metallic layer on at least a portion of the detection layer, the semi-reflective metallic layer comprising palladium and having a network of fine irregular cracks therein; and heating the detection layer and semi-reflective metallic layer in the presence of molecular oxygen at a temperature sufficient to cause the cracks to widen. Sensors prepared according to method are also disclosed.

21 Claims, 1 Drawing Sheet

U.S. PATENT DOCUMENTS

2005/0136231 A1 6/2005 Voss-Kehl et al.
2005/0181198 A1 8/2005 David et al.

FOREIGN PATENT DOCUMENTS

| JP | 2002-54990 A | 2/2002 |
|---|---|---|
| WO | WO 04/000549 A1 | 12/2003 |
| WO | WO 2005/012397 A2 | 2/2005 |

OTHER PUBLICATIONS

Budd et al., "Solution-Processed, Organophilic Membrane Derived from a Polymer of Intrinsic Microporosity", Advanced Materials, Mar. 5, 2004, vol. 16, No. 5, pp. 456-459.

Budd et al., "Free volume and intrinsic microporosity in polymers", J. Mater. Chem., 2005, vol. 15, pp. 1977-1986.

Budd et al., "Polymers of intrinsic microporosity (PIMS): robust solution-processable, organic nanoporous materials", Chem. Commun., 2004, pp. 230-231.

Product Information: DuPont® Teflon® AF amorphous fluoropolymers, 4 pages, Feb. 1998.

David et al., "Plasma Deposited Microporous Analyte Detection Layer", U.S. Appl. No. 11/275,277, filed Dec. 21, 2005.

Padiyath et al., "Solar Control Multilayer Film", U.S. Appl. No. 11/313,518, filed Dec. 21, 2005.

Babu et al., "Two-step regression procedure for the optical characterization of thin films", Applied Optics, Mar. 1, 1991, vol. 30, No. 7, pp. 839-846.

OPTOCHEMICAL SENSOR AND METHOD OF MAKING THE SAME

BACKGROUND

There are various sensors for detecting the presence of a volatile organic compound (i.e., VOC). Optochemical sensors use electromagnetic radiation to detect the presence of VOCs, for example, by measuring changes in the optical properties of a sensor material upon exposure to a VOC.

As a general rule, the response time of such sensors depends, at least in part, on the rate at which a VOC may be absorbed into, or adsorbed onto the surfaces of, the sensor material. Materials that are known to be useful as sensing materials in optochemical sensors include those known variously in the art as "polymers of intrinsic microporosity" or as "intrinsically microporous polymers." Intrinsically microporous polymers are typically characterized by poor packing efficiency, giving a structure in the solid state that has a large pore volume. Volatile compounds can typically be sorbed within these pores, making such materials of interest in sensor applications.

SUMMARY

In one aspect, the present invention provides a method of making an optochemical sensor, the method comprising:

providing a reflective substrate having a major surface;

affixing a detection layer comprising at least one intrinsically microporous polymer to at least a portion of the major surface;

depositing a substantially continuous semi-reflective metallic layer on at least a portion of the detection layer, the semi-reflective metallic layer comprising palladium and having a network of fine irregular cracks therein; and heating at least the detection layer and semi-reflective metallic layer in the presence of molecular oxygen at a temperature sufficient to cause the cracks to widen.

In some embodiments, heating the detection layer and semi-reflective metallic layer at a temperature sufficient to cause the cracks to widen also causes the at least one intrinsically microporous polymer to form protrusions that extend from the detection layer through the metallic layer.

The method typically increases the permeability of the outermost layer, allowing example VOCs to be more readily sorbed by the detection layer, thereby making it advantageous for use in sensors.

Accordingly, in another aspect, the present invention provides an optochemical sensor comprising:

a reflective substrate having a major surface;

a detection layer disposed on at least a portion of the major surface of the reflective substrate, the detection layer comprising at least one intrinsically microporous polymer; and a substantially continuous semi-reflective metallic layer disposed on at least a portion of the detection layer, wherein the semi-reflective metallic layer comprises palladium, and wherein the semi-reflective metallic layer has a network of fine irregular cracks therein.

As used herein:

"analyte" means a specific component that is being detected in a chemical analysis;

"optical thickness" as it refers to the detection layer means the product of its physical thickness and its refractive index;

"organic" means containing carbon;

"reflective" means semi-reflective or fully reflective; and

"semi-reflective" means neither fully reflective nor fully transmissive, for example, about 20 to about 90 percent reflective, or about 30 to about 70 percent reflective.

Throughout the present application the term "microporous" is intended to broadly encompass materials which may also be described as "nanoporous".

DETAILED DESCRIPTION

Figure 1A:
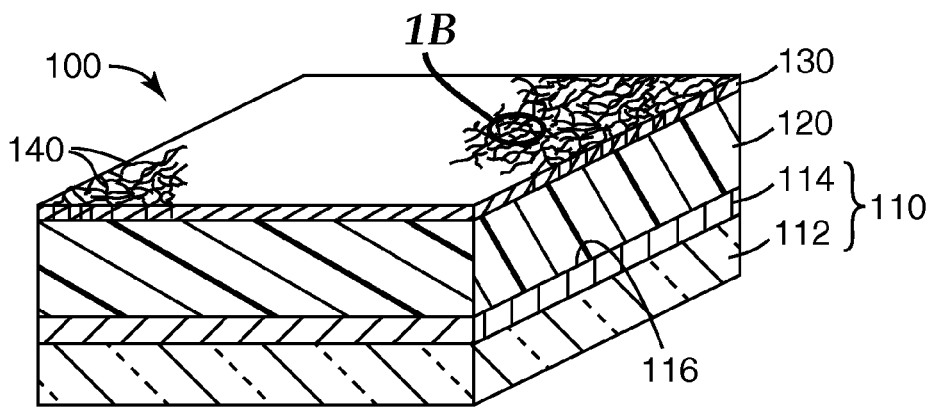
FIG. 1A is a perspective view of an exemplary sensor according to the present invention.
Figure 1B:
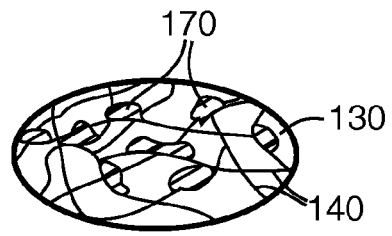
FIG. 1B is an enlarged perspective view of a portion of semi-reflective metallic layer 130 of FIG. 1A.

An exemplary optochemical sensor prepared according to the present invention is shown in FIG. 1A. Referring now to FIG. 1A, optochemical sensor 100 comprises reflective substrate 110 having major reflective surface 116. In some embodiments, reflective substrate 110 comprises optional base 112 having optional reflective layer 114 thereon. Detection layer 120 comprises an intrinsically microporous polymer disposed on at least a portion of surface 116. Semi-reflective metallic layer 130, which comprises palladium metal, is disposed on at least a portion of layer 120, and has a network of fine cracks 140 therein. Protrusions 170 (shown in FIG. 1B) extend from detection layer 120 through semi-reflective metallic layer 130.

The reflective substrate may be any substrate that has a reflective surface. The reflective substrate may be a unitary body, and may be relatively thick or thin. Examples of unitary reflective substrates include reflective metal foils or sheets. Optionally, the reflective substrate may comprise a base having a reflective layer thereon.

If present, the base may comprise any suitable material capable of providing support for the optional reflective layer. It may be flexible or nonflexible. The base material can be tailored to the application. Typically, it is suitable to use in a vacuum deposition process. Exemplary bases include polymeric films, glass, ceramics, and metal. The base material may be made permeable to analyte by being designed to contain an array of holes through which analyte can pass. Further, the base material may be a woven or nonwoven material, a mesh, or a filter membrane through which analyte can pass.

The reflective substrate (e.g., including an optional reflective layer) may comprise any material that can form a reflective layer. Typically, the material is fully reflective at a thickness of about 20 to about 200 nm, although other thicknesses may also be used. For example, thinner layers of material can typically be used to make the reflective layer semi-reflective. Exemplary suitable materials include metals and semi-metals such as aluminum, chromium, gold, nickel, titanium, palladium, platinum, silicon, and silver. Combinations of metals and/or semi-metals may also be used (e.g., such as gold-palladium or nickel-chromium). Other suitable materials that may be included in the reflective substrate include reflective metal oxides such as, for example, chromium oxide and titanium oxide. Although the reflective substrate is typically made to be more reflective than the semi-reflective layer, sometimes it is desirable to have the reflectivity of the reflective layer and semi-reflective layer be the same; for example, so a response to the presence of an analyte can be seen from either side of the sensor film. In some embodiments, the reflective substrate may also be etched or perforated to create holes or other open areas through which analyte can penetrate into the detection layer, although this is not a requirement.

In some exemplary embodiments of the present invention, the optional reflective layer is at least about 90 percent reflective (i.e., at least about 10 percent transmissive), and in some embodiments, about 99 percent reflective (i.e., about 1 percent transmissive). In other exemplary embodiments of the present invention, the optional reflective layer is a semi-reflective layer, wherein the reflective layer is at least about 20 percent reflective, such as about 20 to about 90 percent reflective, or about 30 to about 70 percent reflective.

The detection layer comprises one or more intrinsically microporous polymers that undergo a change in optical thickness (which depends on physical thickness (d) and refractive index (n) of the detection layer wherein optical thickness=n·d) upon uptake of an analyte, which results in a change in the observed color of light reflected by the sensor as compared to light reflected by the sensor in the absence of the analyte.

The detection layer may optionally comprise two or more sublayers. One or more of the optional sublayers may be discontinuous or patterned. The optional sublayers may comprise different polymeric materials and may adsorb different analytes and/or may have different degrees of sensitivity to one or more analytes. The optional sublayers may have a variety of configurations; for example, they may be stacked or may be side by side.

In some embodiments, at least one optional sublayer may comprise inorganic materials such as, for example, transparent and metal oxides, nitrides, and oxynitrides of appropriate thickness for producing color by optical interference. Specific examples of suitable inorganic materials include, silicon oxides, silicon nitrides, silicon oxynitrides, aluminum oxides, titanium oxides, titanium nitride, titanium oxynitride, tin oxides, zirconium oxides, and combinations thereof. Other inorganic materials, such as zeolites, are also suitable for use in sublayer(s). Optional sublayer(s) may be microporous, porous or nonporous.

Further materials that may be included in at least one optional sublayer include amorphous random covalent network thin films as disclosed in U. S. Pat. Appln. Publ. No. 2007/0141580 A 1 (David et al.), the disclosure of which is incorporated herein by reference.

Typically, the physical thickness of the detection layer is in a range of from about 150 to about 1200 nanometers, for example, in a range of from about 500 to about 900 nanometers, although thinner and thicker detection layers may also be used.

The thickness of the detection layer may be patterned. This may be desirable when the sensor is designed so that the presence of an analyte causes a change in the refractive index of the detection layer, thereby making a pattern disappear (for example, when one portion changes optical thickness to be the same optical thickness as an adjacent portion) or appear (for example, when a portion undergoes an optical thickness change so as to have a different optical thickness than an adjacent portion).

The detection layer may further comprise additional polymer components; for example, a homogeneous or heterogeneous blend with at least one of the components being an intrinsically microporous polymer.

As used herein, the term "intrinsically microporous polymer" means an organic polymer that has microporosity due to its molecular structure rather than from processing or a templated preparation. Further, intrinsically microporous polymers have a free volume of at least 10 percent; for example, at least 15 percent or even at least 30 percent.

As applied to polymers, the term "free volume" refers to the volume of a polymer not actually occupied by molecules of the polymer. Free volume that is accessible by gaseous species may be readily determined by various known methods including, for example, gas adsorption techniques coupled with Brunauer-Emmett-Teller (BET), Barrett-Joyner-Halenda (BJH), or Horvath-Kawazoe analysis. For example, details concerning gas adsorption techniques are reported by S. J. Gregg and K. S. W. Sing in "Adsorption, Surface Area, and Porosity", $2^{nd}$ Edition, Academic Press: London (1982).

Typically, useful intrinsically microporous polymers, whether taken alone or as a combination thereof, have a total accessible pore volume as measured by gas adsorption of at least 0.1 cc/g (0.1 milliliters per gram), for example, at least 0.2 cc/g (0.2 milliliters per gram) or even at least 0.5 cc/g (0.5 milliliters per gram), although values outside of the range may also be used. Further, it is found that useful results are obtained from those intrinsically microporous polymers that have at least 25 percent of the total pore volume as measured by gas adsorption from pores with average diameters in a range of from 0.3 nanometer to 20 nanometers, although distributions of pore sizes outside may also by used.

Many intrinsically microporous polymers are known. For example, in *Chemical Communications*, 2004, (2), pp. 230-231, Budd et al. report a series of intrinsically microporous materials containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1.

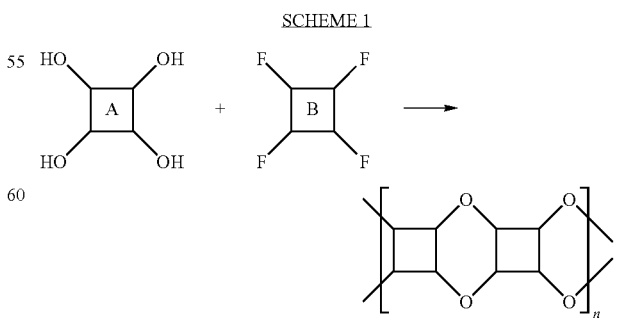

SCHEME 1

TABLE 1

| COMPONENT A | COMPONENT B |
|---|---|
| A1 (5,5',6,6'-tetrahydroxy-3,3,3',3'-tetramethyl-1,1'-spirobisindane) | B1 (tetrafluoroterephthalonitrile) |
| A2 (dihydroxy binaphthyl) | B2 (octafluorobiphenyl) |
| A3 (tetrahydroxybenzene) | B3 (decafluorobenzophenone) |

Further suitable Components A and B, and resultant intrinsically microporous polymers, are known in the art, for example, as reported by Budd et al. in *Journal of Materials Chemistry*, 2005, Vol. 15, pp. 1977-1986 and by McKeown et al. in *Chemistry, A European Journal*, 2005, Vol. 11, 2610 -2620, and in PCT Published Application WO 2005/012397 A2 (McKeown et al.)

Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

Intrinsically microporous polymers are typically soluble in organic solvents such as, for example, tetrahydrofuran and can thus be cast as films from solution (e.g., by spin-coating, dip coating, or bar coating). However, it is discovered that the characteristics (accessible thicknesses, optical clarity, and/or appearance) of films made from solutions of these polymers may vary markedly depending on the solvent or solvent system used to cast the film. For example, intrinsically microporous polymers of higher molecular weights may need to be cast from relatively unusual solvents (e.g., cyclohexene oxide or tetrahydropyran) to generate films with desirable properties for use in optochemical sensors as described herein. In addition to solution coating methods, the detection layer may be applied to the reflective substrate by any other suitable method.

The detection layer and/or intrinsically microporous polymers may be crosslinked if desired, for example, by high-energy radiation.

The reflective and semi-reflective layers may be formed on the detection layer by standard vapor coating techniques such as evaporation, sputtering, chemical vapor deposition (CVD), plasma deposition, flame deposition, or any other technique provided that the technique selected to make the semi-reflective layer results in a substantially continuous semi-reflective layer that has a network of fine cracks. The reflective and semi-reflective layers may be made using the same or different techniques.

According to the present invention, it is discovered that heat treatment of intrinsically microporous polymers can dramatically improve their performance in optochemical sensors, for example, as described herein.

The semi-reflective metallic layer comprises palladium either as a pure metal or in combination with one or more additional metals or semi-metals such as, for example, copper, mercury, silicon, aluminum, rhodium, iridium, nickel, chromium, osmium, gold, or silver.

The semi-reflective metallic layer forms a permeable, substantially continuous layer that has a different index of refraction than the detection layer. In general, the semi-reflective metallic layer may have any thickness as long as it remains semi-reflective and has a network of fine cracks. Typically, these properties are achieved at a thickness of from about 3 to about 10 nanometers, although other thickness may also be used. Desired thicknesses will typically depend on the material used to form the layer, the material onto which the layer is deposited, the analyte to be detected, and the medium that will carry the analyte.

The optochemical sensor may comprise additional layers between any of the previously described elements, as long as any additional layers do not significantly and adversely affect the optics of the sensor. Exemplary additional layers include tie layers and structural layers.

Optochemical sensors according to the present invention may be fabricated generally according to the procedures set forth in U.S. Publ. Pat. Appln. No. 2004/0184948 A1 (Rakow et al.), the disclosure of which is incorporated herein by reference, with the additional step of heating the detection layer and semi-reflective metallic layer in the presence of molecular oxygen at a temperature sufficient to cause the cracks to widen. Typically, heating in an oven at a temperature in a range of from about 200 to about 225° C. for a period of at least about 30 minutes is effective, although other temperatures and durations may also be used. At temperatures of 250° C. or higher, polymer decomposition may occur to a large degree and become a problem.

Optochemical sensors according to the present invention are useful for calculating or estimating the concentration of an analyte, for example, from a response observed from the sensor when it is exposed to the analyte. The analyte may be, for example, a gas (e.g., organic vapor) or a liquid.

Sensor responses are typically calorimetric in nature (e.g., as an observed color change) although other responses may also be useful. For example, the optochemical sensors may be used in a system comprising the sensor, a light source, and, optionally, a means of monitoring the sensor for a change of color or a change in spectral peak position or intensity. Sensors of the present invention may typically be conveniently monitored by reflectance spectroscopy. The light source could be a natural or artificial light source. The monitoring could be done in a variety of ways. It could be done visually, with a photo-detector, or by other suitable means.

Two or more optochemical sensors may be combined to form an array. The array may be in any suitable configuration. For example an array may comprise two or more sensors side by side, or sensors may be attached to, or constructed on, opposite sides of a substrate. The sensors may be of the same type or may be different.

In at least one embodiment, the analyte is detected by a change in optical thickness of the detection layer upon exposure to the analyte. Such changes are typically observable in the visible light range and can often be detected by the unaided human eye. However, sensors can be designed such that a change in optical thickness can be detected when subjected to other light sources such as UV, infrared, or near infrared. Various detection mechanisms can also be used. Examples of suitable detection mechanisms include spectrophotometers, fiber optic spectrophotometers, and photo-detectors, e.g., charge coupled devices (ccd), digital cameras, etc.

Objects and advantages of this invention are further illustrated by the following non-limiting examples, but the particular materials and amounts thereof recited in these examples, as well as other conditions and, details, should not be construed to unduly limit this invention.

EXAMPLES

Unless otherwise noted, all parts, percentages, ratios, etc. in the examples and the rest of the specification are by weight, and all solvent and reagents used in the examples were obtained, or are available, from general chemical suppliers such as, for example, Sigma-Aldrich Company, Saint Louis, Mo., or may be synthesized by conventional methods.

TABLE OF ABBREVIATIONS

| ABBREVIATION | DESCRIPTION |
| --- | --- |
| BC | bis-catechol; 5,5',6,6'-tetrahydroxy-3,3,3'3'-tetramethyl-1,1'-spirobisindane |
| FA | fluorinated arene; tetrafluoroterephthalonitrile |
| DMF | N,N-dimethylformamide |
| THF | tetrahydrofuran |

Test Methods

Surface Area and Pore Volume Measurement

Total pore volume was measured by nitrogen adsorption using a gas adsorption analyzer available under the trade designation "QUANTACHROME AUTOSORB 1C" (Quantachrome Instruments, Boynton Beach, Fla.) operated according to the manufacturer's directions using a 75 point micro pore analysis.

Preparative Examples P1-P5

Polymers were prepared from monomers BC and FA generally according to the procedure reported by Budd et al. in *Advanced Materials,* 2004, Vol. 16, No. 5, pp. 456-459, using the reagents, conditions and polymer descriptions shown in Table 2 (below).

TABLE 2

| Preparative Example | BC, g | FA, g | $K_2CO_3$, g | DMF, mL | Temperature, °C. | Reaction Time, hours | Molecular Weight $M_w$, g/mole | BET Surface area, $m^2/g$ | Total Pore Volume, mL/g |
| --- | --- | --- | --- | --- | --- | --- | --- | --- | --- |
| P1 | 2.25 | 1.32 | 4.5 | 30 | 70 | 24 | 6150 | 728 | 1.298 |
| P2 | 10.25 | 6.02 | 25.7 | 200 | 65 | 72 | 61900 | 817 | 0.687 |
| P3 | 9.0 | 5.28 | 18.0 | 120 | 70 | 24 | 5770 | NM | NM |

TABLE 2-continued

| Preparative Example | BC, g | FA, g | $K_2CO_3$, g | DMF, mL | Temperature, °C. | Reaction Time, hours | Molecular Weight $M_w$, g/mole | BET Surface area, $m^2/g$ | Total Pore Volume, mL/g |
|---|---|---|---|---|---|---|---|---|---|
| P4 | 1.52 | 0.88 | 2.9 | 20 | 70 | 24 | 9700 | NM | NM |
| P5 | 9.0 | 5.28 | 18.0 | 120 | 70 | 24 | 61800 | NM | NM |

In Table 2:
"NM" means not measured, and "Total pore volume" refers to pores with average diameter of less than 370 nanometers.

Each polymer was dissolved in THF, precipitated three times from methanol, and then dried under vacuum at room temperature. In each case, a bright yellow solid was obtained.

Examples 1-4 and Comparative Examples C1-C3

Glass slides having a 100 nanometer thick coating of aluminum were used as the reflective substrate. The polymer from Preparative Example P1 was dissolved in THF to give a 3 percent by weight solution, which was spin coated onto the aluminum at the speed shown in Table 3. After spin coating, a 5-nanometer (nm) thick Au/Pd (60:40 Au to Pd by weight) layer was sputter coated onto the polymer. Samples thus prepared were heated in air in a belt furnace for 30 minutes according to the temperature shown in Table 3 (below) to form optochemical sensors, and any color change in the polymer layer was noted.

TABLE 3

| Example | Spin Coating Speed, rpm | Peak Heating Temperature, °C. | Initial Color | Color After Heating |
|---|---|---|---|---|
| Comparative C1 | 1000 | not heated | purple | not applicable |
| Comparative C2 | 1000 | 150 | purple | purple |
| Comparative C3 | 2000 | 150 | gold | gold |
| 1 | 1000 | 200 | purple | yellow |
| 2 | 2000 | 200 | gold | blue |
| 3 | 1000 | 250 | purple | dull yellow |
| 4 | 2000 | 250 | gold | dull yellow |

UV/VIS reflectance spectroscopy of the heated samples showed that samples heated at 250° C. showed a loss of defined peaks in the UV/VIS reflectance spectrum, while samples heated at 200° C. showed large shifts in the reflectance wavelength maxima.

Figure 2:
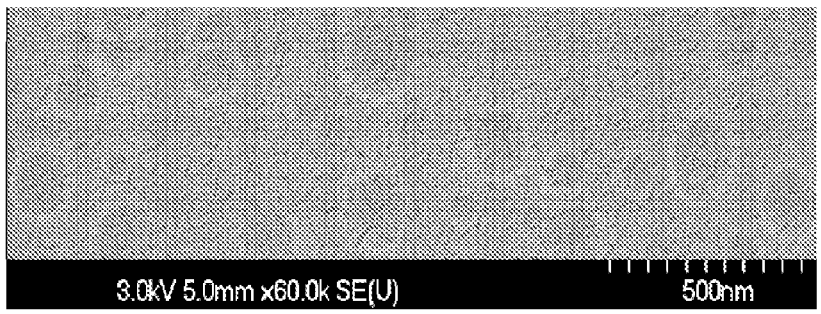
FIG. 2 is a scanning electron micrograph of the surface of a Pd—Au metallic layer of an exemplary optochemical sensor prepared according to the procedure of Example 1 before heat treatment.

FIG. 2 is an electron micrograph of a replicate of Example 1, prior to heating, taken at a magnification of 60,000×.

Figure 3:
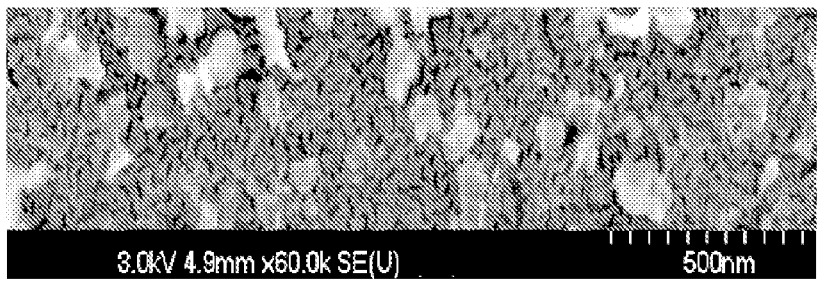
FIG. 3 is a scanning electron micrograph of the surface of a Pd—Au metallic layer of an exemplary optochemical sensor prepared according to the procedure of Example 1 after heat treatment.

FIG. 3 is an electron micrograph of a replicate of Example 1, after heating, taken at a magnification of 60,000×.

Example 5

The multilayered film sample of Example 1 was tested for response to low concentrations of toluene vapor. A red shift in reflectance peak wavelength maximum of 5 nanometers was observed at 50 parts per million (ppm) of toluene vapor, and a red shift in reflectance peak wavelength maximum of approximately 50 nm was observed at 2000 ppm concentration.

Comparative Example C4

Example 5 was repeated except that the multilayer film of Comparative Example 1 was used instead of the multilayer film of Example 1. No shift position of the reflectance peak wavelength maximum was observed for this film at concentrations of 2000 ppm of toluene vapor and below.

Comparative Examples C5 and C6

Two multilayer film assemblies were prepared. Glass slides containing a 100-nanometer thick layer of aluminum were used as the base substrates. The polymer from Preparative Example P3 was dissolved in THF to give a 5 percent by weight solution that was spin coated onto the aluminum at 1000 rpm. After spin coating, a 5-nm thick Al layer was evaporatively deposited onto the polymer in both assemblies. Both coated assemblies were characterized by a yellow-red hue after metal coating. Comparative Example C5 was heated in a belt furnace for 30 minutes at 200° C., which did not result in a change in the yellow-red hue. Comparative Example C6 was not heat processed. Comparative Examples C5 and C6 were tested for their response to low concentrations of toluene vapor; neither sensor showed a change in reflectance spectrum response for concentrations as high as 2000 ppm of toluene vapor.

Comparative Examples C7 and C8

Two multilayer film assemblies were prepared. Glass slides containing a 100-nanometer thick layer of aluminum were used as the base substrates. The polymer from Preparative Example P3 was dissolved in THF to give a 5 percent by weight solution that was spin coated onto the aluminum at 1000 rpm. After spin coating, a 5-nm thick Ti layer was evaporatively deposited onto the polymer in both assemblies. Both coated assemblies were characterized by a yellow-red hue after metal coating. Comparative Example C7 was heated in a belt furnace for 30 minutes at 200° C., which did not result in a change in the yellow-red hue. Comparative Example C8 was not heat processed. Comparative Examples C7 and C8 were tested for their response to low concentrations of toluene vapor. Neither of Comparative Examples C7 and C8 showed a change in reflectance spectrum response for concentrations as high as 2000 ppm toluene vapor.

Comparative Examples C9 and C10

Two multilayer film assemblies were prepared. Glass slides containing a 100 nanometer thick layer of aluminum were used as the base substrates. The polymer from Preparative Example P4 was dissolved in THF to give a 5 percent by weight solution that was spincoated onto the aluminum at 1500 rpm. After spin coating, a 5-nm thick chromium layer was evaporatively deposited onto the polymer of each assembly. Both coated assemblies were characterized by a yellow-green hue after metal coating. Comparative Example C9 was heated in a belt furnace for 30 minutes at 200° C., which did not result in a change in the yellow-green hue. Comparative Example C10 was not heat processed. Comparative Examples C9 and C10 were tested for their responses to low concentrations of toluene vapor. Neither of Comparative Examples C9 and C10 showed a change in reflectance spectrum response for concentrations as high as 2000 ppm of toluene vapor.

Example 6 and Comparative Example C11

Two multilayer film assemblies were prepared. Glass slides containing a 100 nanometer thick layer of aluminum were used as the base substrates. The polymer from Preparative Example P5 was dissolved in chlorobenzene to give a 4 percent by weight solution that was spin coated onto the substrates at 3000 rpm. After spin coating, a palladium layer was sputter coated (5 nm approximate thickness) onto the polymer layer in both assemblies. The coated assemblies were characterized by a blue-green color after Pd metallization. Example 6 was heated in a belt furnace for 30 minutes at 200° C., which resulted in a color change to give a yellow-green hue. Comparative Example C11 was not heat processed. Example 6 and Comparative Example C11 were tested for their responses to concentrations of toluene vapor. Example 6 gave an observable response in its visible reflectance spectrum at 2000 ppm of toluene vapor, while Comparative Example C11 gave no response up to 2000 ppm of toluene vapor.

Comparative Examples C12 and C13

Two multilayer film assemblies were prepared. Glass slides containing a 100 nanometer thick layer of aluminum were used as the base substrates. The polymer from Preparative Example P5 was dissolved in chlorobenzene to give a 4 percent by weight solution that was spin coated onto the aluminum at 3000 rpm. After spin coating, a nickel layer was sputter coated (5 nm approximate thickness) onto the polymer layer in both assemblies. Both coated assemblies were characterized by a yellow-green hue after metal coating. Comparative Example C12 was heated in a belt furnace for 30 minutes at 200° C., which did not result in a change in the yellow-green hue. Comparative Example C13 was not heat processed. Comparative Examples 12 and 13 were tested for their responses to low concentrations of toluene vapor. Neither of Comparative Examples C12 and C13 showed a change in reflectance spectrum response for concentrations as high as 2000 ppm of toluene vapor.

Various modifications and alterations of this invention may be made by those skilled in the art without departing from the scope and spirit of this invention, and it should be understood that this invention is not to be unduly limited to the illustrative embodiments set forth herein.

What is claimed is:

1. A method of making an optochemical sensor, the method comprising:
   providing a reflective substrate having a major surface;
   affixing a detection layer comprising at least one intrinsically microporous polymer to at least a portion of the major surface;
   depositing a substantially continuous semi-reflective metallic layer on at least a portion of the detection layer, the semi-reflective metallic layer comprising gold/palladium alloy and having a network of fine irregular cracks therein; and
   heating at least the detection layer and semi-reflective metallic layer in the presence of molecular oxygen at a temperature sufficient to cause the cracks to widen.

2. A method according to claim 1, further comprising causing the at least one intrinsically microporous polymer to form protrusions that extend from the detection layer through the semi-reflective metallic layer.

3. A method according to claim 1, further comprising:
   exposing the optochemical sensor to organic vapor; and
   observing a response of the optochemical sensor to the exposure.

4. A method according to claim 3, further comprising:
   calculating or estimating the concentration of the organic vapor.

5. A method according to claim 4, wherein observing a response comprises reflectance spectroscopy.

6. A method according to claim 1, wherein the detection layer comprises at least one polymer having dibenzodioxane linkages.

7. A method according to claim 1, wherein the detection layer has a thickness in a range of from about 150 nanometers to about 1200 nanometers.

8. A method according to claim 1, wherein the semi-reflective metallic layer has a thickness in a range of from about 3 nanometers to about 10 nanometers.

9. A method according to claim 1, wherein the semi-reflective metallic layer further comprises an additional metal or semi-metal.

10. A method according to claim 1, wherein the reflective substrate comprises a base having a reflective layer thereon that comprises the reflective surface.

11. A method according to claim 10, wherein the base is permeable.

12. A method according to claim 10, wherein the base is selected from the group consisting of a woven material, a nonwoven material, a mesh, and a filter membrane.

13. A method according to claim 1, wherein the at least one intrinsically microporous polymer has a total pore volume as measured by gas adsorption of at least 0.1 milliliters per gram, and wherein at least 25 percent of the total pore volume results from pores with average diameters in a range of from 0.3 to 20 nanometers.

14. An optochemical sensor comprising:
   a reflective substrate having a major surface;
   a detection layer disposed on at least a portion of the major surface of the reflective substrate, the detection layer comprising at least one intrinsically microporous polymer; and
   a substantially continuous semi-reflective metallic layer disposed on at least a portion of the detection layer, wherein the semi-reflective metallic layer comprises gold/palladium alloy, wherein the semi-reflective metallic layer has a network of fine irregular cracks therein, and wherein there exist a plurality of protrusions as a result of heating that extend from the detection layer through the semi-reflective metallic layer.

15. A sensor according to claim 14, wherein the reflective substrate comprises a base having a reflective layer thereon that comprises the reflective surface, and wherein the detection layer is affixed to at least a portion of the reflective layer.

16. A sensor according to claim 15, wherein the base is permeable.

17. A sensor according to claim 16, wherein the base is selected from the group consisting of a woven material, a nonwoven material, a mesh, and a filter membrane.

18. A sensor according to claim 14, wherein the semi-reflective metallic layer has a thickness in a range of from about 5 nanometers to about 10 nanometers.

19. A sensor according to claim 14, wherein the detection layer comprises at least one polymer having dibenzodioxane linkages.

20. A sensor according to claim 14, wherein the detection layer has a thickness in a range of from about 150 nanometers to about 1200 nanometers.

21. A sensor according to claim 14, wherein the at least one intrinsically microporous polymer has a total pore volume as measured by gas adsorption of at least 0.1 milliliters per gram, and wherein at least 25 percent of the total pore volume results from pores with average diameters in a range of from 0.3 to 20 nanometers.

* * * * *